US012791562B2

United States Patent

Chau et al.

(10) Patent No.: US 12,791,562 B2

(45) Date of Patent: Nov. 10, 2026

(12) United States Patent

(54) SYSTEM AND METHOD FOR DETERMINING A CONCENTRATION OF AN ANALYTE IN A FLUID

(71) Applicant: AUSMED GLOBAL LIMITED, Hong Kong (CN)

(72) Inventors: Li Yin Chau, Hong Kong (CN); Yuk Sum Wong, Hong Kong (CN); Lam Christine Yip, Hong Kong (CN)

(73) Assignee: AUSMED GLOBAL LIMITED, Hong Kong (CN)

( * ) Notice: Subject to any disclaimer, the term of this patent is extended or adjusted under 35 U.S.C. 154(b) by 510 days.

(21) Appl. No.: 18/264,795

(22) PCT Filed: Feb. 12, 2021

(86) PCT No.: PCT/IB2021/051152

§ 371 (c)(1),
(2) Date: Aug. 9, 2023

(87) PCT Pub. No.: WO2022/172059

PCT Pub. Date: Aug. 18, 2022

(65) Prior Publication Data

US 2024/0110919 A1 Apr. 4, 2024

(51) Int. Cl.

*G01N 33/64* (2006.01)
*A61B 5/08* (2006.01)
*G01N 21/78* (2006.01)

(52) U.S. Cl.

CPC ............ *G01N 33/64* (2013.01); *A61B 5/082* (2013.01); *G01N 21/78* (2013.01)

(58) Field of Classification Search

CPC ...... G01N 33/64; G01N 21/78; G01N 21/272; G01N 21/80; G01N 33/4975; G01N 2800/042; G01N 33/52; G01N 33/497; G01N 31/22; A61B 5/082

See application file for complete search history.

(56) References Cited

U.S. PATENT DOCUMENTS

| | | | |
|---|---|---|---|
| 4,931,404 | A | 6/1990 | Kundu |
| 2004/0043527 | A1 | 3/2004 | Bradley et al. |
| 2007/0048180 | A1 | 3/2007 | Gabriel et al. |

(Continued)

FOREIGN PATENT DOCUMENTS

| | | | |
|---|---|---|---|
| BR | 8704258 | A | 4/1988 |
| CN | 110431418 | A | 11/2019 |

(Continued)

OTHER PUBLICATIONS

International Search Report and Written Opinion for PCT/1B2021/051152 dated Nov. 11, 2021.

(Continued)

*Primary Examiner* — Jennifer Wecker
*Assistant Examiner* — Tracy Ching-Tian Colena
(74) *Attorney, Agent, or Firm* — Bryan D. Zerhusen; Nicholas R. Herrel; CANTOR COLBURN LLP

(57) ABSTRACT

Disclosed herein is a method for determining a concentration of an analyte in a fluid and a system that uses the method. The method comprises exposing a sorbent material having a hydroxylamine salt and a halochromic indicator sorbed thereon and/or therein to the fluid, and determining the concentration of analyte using the change of colour, or rate of change of colour of the sorbent material.

18 Claims, 5 Drawing Sheets

(56) References Cited

U.S. PATENT DOCUMENTS

| | | | |
|---|---|---|---|
| 2009/0049890 | A1 | 2/2009 | Zhong et al. |
| 2012/0156099 | A1 | 6/2012 | Zhong et al. |
| 2016/0033450 | A1 | 2/2016 | Blauw et al. |
| 2017/0284999 | A1 | 10/2017 | Maric et al. |
| 2018/0056302 | A1 | 3/2018 | Ahmad et al. |
| 2019/0094146 | A1 | 3/2019 | Tao et al. |

FOREIGN PATENT DOCUMENTS

| | | | |
|---|---|---|---|
| CN | 110554032 | A | 12/2019 |
| CN | 111344552 | A | 6/2020 |
| EP | 3260860 | A1 | 12/2017 |
| JP | S6375561 | A | 4/1988 |
| JP | 6171470 | B2 | 7/2017 |
| SU | 728083 | A1 | 4/1980 |
| SU | 877425 | A1 | 10/1981 |
| SU | 958930 | A1 | 9/1982 |
| SU | 1109640 | A1 | 8/1984 |
| WO | 2011147425 | A1 | 12/2011 |
| WO | 2018027309 | A1 | 2/2018 |
| WO | 2018081877 | A9 | 5/2019 |
| WO | 2020047606 | A1 | 3/2020 |

OTHER PUBLICATIONS

Supplementary European Search Report for EP21925547 dated Oct. 1, 2024.

Wang, D., et al., Colorimetric Sensor for Online Accurate Detection of Breath Acetone, ACS Sensors, 2021, 6, 450-453 (Published Nov. 19, 2020).

Choi SJ, Selective diagnosis of diabetes using Pt-functionalized WO3 hemitube networks as a sensing layer of acetone in exhaled breath. Anal Chem. Feb. 5, 2013;85(3):1792-6. doi: 10.1021/ac303148a. Epub Jan. 7, 2013. PMID: 23252728.

SYSTEM AND METHOD FOR DETERMINING A CONCENTRATION OF AN ANALYTE IN A FLUID

CROSS-REFERENCE TO RELATED APPLICATIONS

The present application is a National Stage entry of International Patent Application No. PCT/IB2021/051152, filed 12 Feb. 2021 and published as International Patent Application Publication No. WO 2022/172059 A1, which is incorporated by reference herein in its entirety for all purposes.

FIELD

The invention relates to a system and method for determining a concentration of an analyte in a fluid.

BACKGROUND

Systems comprising sensors are used to sense various analytes for a variety of applications. These analytes may be biomarkers, contaminants, narcotics, or any other species where there is an interest in their detection and/or quantification. Such analytes may, for example, be biomarkers, where their presence, absence, or concentration in a sample may be indicative of a disease or condition.

For example, exhaled breath from a human contains a variety of compounds that can be detected for monitoring of disease and/or physiological processes in the subject's body. The acetone concentration in the exhaled breath of a subject is a biomarker that may relate to the rate of transforming fat into energy in the ketosis status, in which, the body also releases acetone, acetoacetic acid and beta-hydroxy butyric acid into the bloodstream in the liver.

A healthy person can achieve ketosis status by undergoing fasting or taking low-carbohydrate or ketogenic diets. For a person that has diabetes, the concentration of acetone will rise in both the blood and exhaled breath when the body does not have sufficient insulin. A continuous rise of ketone bodies in the blood may lead to ketoacidosis.

Detection of acetone concentration in the exhaled breath is a non-invasive approach in determining whether the healthy person is in the ketosis status. Detection of acetone concentration in the exhaled breath can also help diabetes to monitor levels of ketone bodies in the body. Accordingly, there is a need for new and/or improved methods and systems for determining the concentration of an analyte (e.g. acetone) in a fluid, in particular in a breath sample.

A system or method for determining the concentration of an analyte, such as acetone, requires suitable sensitivity for the analyte in order to limit false negative results. For example, the EPA allowable limit for lead in drinking water is 15 ppb. Accordingly, a system or method for determining the concentration of lead in drinking water must be sensitive enough to reliably detect lead at least down to a concentration of 15 ppb.

Additionally, a system or method for determining the concentration of an analyte, such as acetone, must have a suitable level of selectivity to the analyte in order to limit false positive results. For example, a system or method sensitive enough to determine the concentration of lead in drinking water below 15 ppb will be of little use in that application if it has poor selectivity for lead. If the system or method responds similarly to sodium in drinking water, which is typically present in drinking water in much higher concentrations than lead, then such a system or method would yield many false positive results.

Systems or methods in the prior art may have suitable sensitivity, selectivity, precision and/or accuracy for sensing an analyte, but only within a narrow analyte concentration range. However, for many analytes, such as acetone, it is necessary to detect and/or quantify their concentration over a wide variety of concentrations. Accordingly, there is a need to develop systems and methods that have a wide dynamic range and/or a wide working range for determining the concentration of analytes, such as acetone, at a variety of concentrations. Some systems or methods may meet these requirements, but may have a high equipment cost, for example they may require use of a GC-MS. Further, it may be slow to determine an accurate concentration of an analyte using such systems or methods.

Low-cost systems and methods may suffer from one or more of difficult calibration yielding poor accuracy, poor repeatability yielding poor precision, poor selectivity, poor sensitivity, a narrow dynamic range and/or a narrow working range. Therefore, there is a need to develop low cost systems and methods having improvements in any one or more of these properties. There is also a need to develop systems and methods suitable for rapid tests.

Systems and methods for determining the concentration of certain biomarkers may only be effective for invasively collected samples, such as blood. For example, systems for determining blood glucose levels for patients with diabetes are accurate and enable quantitative glucose concentration measurement, but only for invasively collected blood samples. Accordingly, there is also a need for systems and methods with improved sensitivity, reliability and/or affordability that enable detection or quantitation of biomarkers, such as acetone, in non-invasively collected samples, for example in urine, saliva, or breath.

It is an aim of the present invention to at least partially satisfy at least one of the above needs.

SUMMARY OF INVENTION

The inventors of the present invention have surprisingly discovered that by utilising a combination of change in colour of a reagent and rate of change in colour of a reagent, it is possible to determine a concentration of an analyte (e.g. acetone) in a fluid across a wide working concentration range.

According to a first aspect there is provided a method of determining a concentration of an analyte in a fluid, said method comprising the following steps:

- providing a sorbent material having a hydroxylamine salt and a halochromic indicator sorbed thereon and/or therein;
- measuring an initial colour value of the sorbent material at an initial time point;
- contacting a fluid with the sorbent material to produce a colour change in the sorbent material;
- measuring a final colour value of the sorbent material at a final time point; and
- determining the concentration of analyte in the fluid by:
  - when a change in colour value of the sorbent material from the initial time point to the final time point is smaller than a threshold colour value:
    - using the change in colour value of the sorbent material from the initial time point to the final time point; and when the change in colour value of the sorbent material from the initial time point to the final time point is greater than or equal to the threshold colour value:

using a rate of change in colour value of the sorbent material over a time range, wherein the time range is between the initial time point and the final time point.

The following options may be used in conjunction with the first aspect, either individually or in any suitable combination.

In certain embodiments, the colour value is an absorbance.

In certain embodiments, the colour value is a wavelength.

In certain embodiments, when the change in colour value of the sorbent material from the initial time point to the final time point is smaller than the threshold colour value, the concentration of analyte is calculated using the equation:

$$AC=M_{CC}*CC+ACI_1$$

wherein AC is the analyte concentration; CC is the change in colour value of the sorbent material from the initial time point to the final time point; and $M_{CC}$ is a slope and $ACI_1$ is a y-intercept, respectively, of a standard plot of colour change value of the sorbent material versus analyte concentration.

In certain embodiments, when the change in colour value of the sorbent material from the initial time point to the final time point is greater than or equal to the threshold colour value, the concentration of analyte is calculated using the equation:

$$AC=M_{CCR}*CCR+ACI_2$$

wherein AC is the analyte concentration; CCR is the rate of change in colour value of the sorbent material over the time range; and $M_{CCR}$ is a slope and $ACI_2$ is a y-intercept, respectively, of a standard plot of rate of colour change value of the sorbent material versus analyte concentration.

In certain embodiments, the threshold colour value is a colour value corresponding to a concentration of analyte of from about 300 to about 400 ppm (v/v) in the fluid.

In certain embodiments, the hydroxylammonium salt is hydroxylammonium chloride.

In certain embodiments, the halochromic indicator is selected from the group consisting of methyl orange, methyl red, methyl yellow, methyl green, methyl violet, chlorophenol red, bromocresol green, conga red, thymol blue, bromophenol blue, cresol red, metacresol purple, malachite green, ethyl violet, crystal violet, 2,4-dinitrophenol, orange IV, erythrosin B, p-(phenylazo)diphenylamine, p-phenylazoaniline and mixtures thereof. In certain embodiments, the halochromic indicator is bromophenol blue.

In certain embodiments, the fluid is breath.

In certain embodiments, the initial and final colour change values of the sorbent material are measured using a photosensor.

In certain specific embodiments, the method comprises:

collecting a fluid sample from a subject in a vessel;

exposing the sorbent material to a light;

measuring the initial colour value of the sorbent material at the initial time point; pumping the fluid through a filter to the sorbent material at a constant flow rate;

measuring a second colour value of the sorbent material at a second time point, the second time point being at a time after the initial time point;

measuring a third colour value of the sorbent material at a third time point, the third time point being at a time after the second time point and before the final time point;

ceasing the pumping; and measuring the final colour value of the sorbent material at the final time point.

In certain embodiments, the analyte is acetone.

In a second aspect there is provided a system for determining a concentration of an analyte in a fluid, said system comprising:

a vessel receiving unit, capable of receiving a fluid sample vessel;

a sorbent material having a hydroxylamine salt and a halochromic indicator sorbed thereon and/or therein;

a pump for pumping a fluid from the fluid sample vessel to the sorbent material;

a light emitting unit for exposing the sorbent material to a light;

a photosensor for measuring a colour value of the sorbent material at an initial time point and a final time point; and a control unit, configured to determine the concentration of analyte in the fluid by:

when a change in colour value of the sorbent material from the initial time point to the final time point is smaller than a threshold colour value:

using the change in colour value of the sorbent material from the initial time point to the final time point; and when the change in colour value of the sorbent material from the initial time point to the final time point is greater than or equal to the threshold colour value:

using a rate of change in colour value of the sorbent material over a time range, wherein the time range is between the initial time point and the final time point.

The following options may be used in conjunction with the second aspect, either individually or in any suitable combination.

In certain embodiments, the pump is capable of pumping the fluid from the fluid sample vessel to the sorbent material at a constant flow rate.

In certain embodiments, the system further comprising a filter for removing moisture from the fluid.

In certain embodiments, the colour value is an absorbance.

In certain embodiments, the colour value is a wavelength.

In certain embodiments, the hydroxylammonium salt is hydroxylammonium chloride.

In certain embodiments, the halochromic indicator is selected from the group consisting of methyl orange, methyl red, methyl yellow, methyl green, methyl violet, chlorophenol red, bromocresol green, conga red, thymol blue, bromophenol blue, cresol red, metacresol purple, malachite green, ethyl violet, crystal violet, 2,4-dinitrophenol, orange IV, erythrosin B, p-(phenylazo)diphenylamine, p-phenylazoaniline and mixtures thereof. In certain embodiments, the halochromic indicator is bromophenol blue.

In certain embodiments, the fluid is breath.

In certain embodiments, the analyte is acetone.

The method of the first aspect may use the system of the second aspect. The system of the second aspect may be used in the method of the first aspect.

In a third aspect there is provided a method of managing diabetes in a patient on a diabetes treatment plan, said method comprising:

determining an acetone concentration of a breath sample of the patient using the method according to the first aspect;

comparing the acetone concentration to a reference acetone concentration range; and if the acetone concentration is outside the acetone concentration reference range, adjusting the diabetes treatment plan.

The method of the third aspect may use the system of the second aspect. The system of the second aspect may be used in the method of the third aspect.

DEFINITIONS

Figure 1:
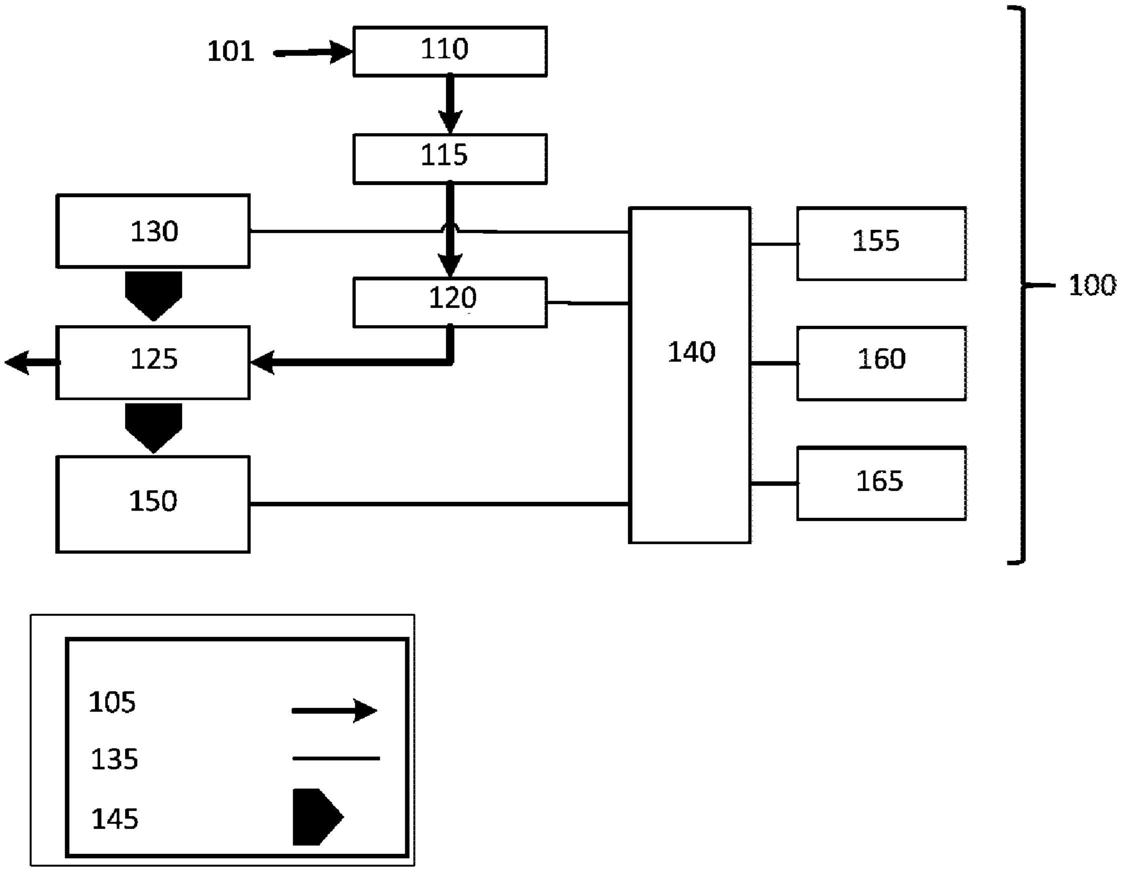
FIG. 1: Schematic diagram of an example system according to specific embodiments of the present invention.

As used herein, the term "about", is relative to the actual value stated, as will be appreciated by those of skill in the art, and allows for approximations, inaccuracies and limits of measurement under the relevant circumstances. Depending on context, it may allow a variation from the stated value of ±10%, ±5%, ±2%, ±1%, ±0.5%, ±0.2%, ±0.1%, ±0.05%, ±0.02%, or ±0.01%.

As used herein, the term "comprising" indicates the presence of the specified integer(s), but allows for the possibility of other integers, unspecified. This term does not imply any particular proportion of the specified integers. Variations of the word "comprising", such as "comprise" and "comprises", have correspondingly similar meanings.

As used herein, the term "accuracy" in reference to a system is a measure of how closely the analyte concentration quantified from the system response agrees with the "true" or expected analyte concentration. Accuracy may be expressed as an absolute error (absolute error=|obtained result-expected result|). It may be expressed as a percentage relative error (percentage relative error=[(|obtained result-expected result|)×100]/expected result). For example, the term "accuracy" in reference to a device, system, sensor or method for determining the concentration of a carbonyl containing compound (e.g. acetone) may be a measure of how closely the carbonyl containing compound concentration quantified using the device, system, sensor, or method respectively agrees with the "true" or expected carbonyl containing compound concentration. Accuracy may be expressed as an absolute error (absolute error=|obtained result-expected result|). It may be expressed as a percentage relative error (percentage relative error=[(|obtained result-expected result|)×100]/expected result).

As used herein, the term "precision" in reference to the system is a measure of the reproducibility and repeatability of the system response at a given analyte concentration. This may be expressed as a percentage relative standard deviation. For example, the term "precision" in reference to a device, sensor, system or method for determining the concentration of an analyte (e.g. acetone) may be a measure of the reproducibility and repeatability of the change in the variable at a given analyte concentration. This may be expressed as a percentage relative standard deviation. In certain embodiments the term "precision" in reference to a device, sensor, system, or method for determining the concentration of an analyte may be a measure of the reproducibility and repeatability of the change in the absorption spectrum of the indicator at a given analyte concentration. This may be expressed as a percentage relative standard deviation.

As used herein, the term "selectivity" in reference to the system for an analyte in a fluid, is a measure of the system's response to the analyte compared with the system's response to a non-analyte component of the fluid. For example, as used herein, the term "selectivity" in reference to a device, sensor, system, or method for determining the concentration of an analyte (e.g. acetone), may be a measure of the change in the variable for an analyte concentration in the fluid compared with another component of the fluid. In certain embodiments the term "selectivity" in reference to a device, system, sensor or method for determining the concentration of an analyte, may be a measure of the change in the absorption spectrum of the indicator for an analyte concentration in the fluid compared with another component of the fluid.

As used herein, the term "dynamic range" in reference to the system is a measure of the concentration range of an analyte in which the system is able to sense or detect the analyte and produce a response that is distinguishable from any background response. For example, the term "dynamic range" in reference to a device, system, sensor or method for determining the concentration of an analyte (e.g. acetone) may be a measure of the concentration range of an analyte in which the device, system, sensor or method is able to produce a change in the variable that is distinguishable from any background change in the variable. In certain embodiments the term "dynamic range" in reference to a device, system, sensor or method for determining the concentration of an analyte may be a measure of the concentration range of an analyte in which the device, system, sensor or method is able to produce a change in the absorption spectrum of the indicator that is distinguishable from any background change in the absorption spectrum of the indicator.

As used herein, the term "working range" in reference to the system is a measure of the concentration range of an analyte in which the analyte concentration can be quantified from the system response. For example, the term "working range" in reference to a device, system, sensor or method for determining the concentration of an analyte (e.g. acetone) may be a measure of the concentration range of an analyte in which analyte concentration can be quantified from the change in the variable. For example, the term "working range" in reference to a device, system, sensor or method for determining the concentration of an analyte may be a measure of the concentration range of an analyte in which the analyte concentration can be quantified from the change in the variable. In certain embodiments, the term "working range" in reference to the device, system, sensor, or method for determining the concentration of an analyte may be a measure of the concentration range of an analyte in which the analyte concentration can be quantified from the change in the absorption spectrum of the indicator.

As used herein, the term "differential response" in reference to the system means that the system can generate more than one response level when exposed to a constant concentration of the analyte. It may mean, for example, that the system can generate different responses at different times after exposure to a constant concentration of the analyte (i.e. temporally differential). Thus, a differential response is a response which varies with a variation in one or more parameters other than analyte concentration, e.g. time from initial exposure to the analyte.

As used herein, the term "configured" means to set up for operation, especially in a particular way.

As used herein, the term "sorbent" means a material capable of adsorbing and/or absorbing a liquid, solid, and/or gaseous compound therein and/or thereon.

As used herein, the term "halochromic" means a material which changes colour when pH changes occur.

As used herein, the term "absorption maximum" means a maximum wavelength and/or intensity of electromagnetic absorption.

DESCRIPTION OF EMBODIMENTS

Disclosed herein is a method of determining a concentration of an analyte in a fluid. The method comprises providing a sorbent material having a hydroxylamine salt and a halochromic indicator sorbed thereon and/or therein; measuring an initial colour value of the sorbent material at an initial time point; contacting a fluid with the sorbent material to produce a colour change in the sorbent material; measuring a final colour value of the sorbent material at a final time point; and determining the concentration of analyte in the fluid by:

- when a change in colour value of the sorbent material from the initial time point to the final time point is smaller than a threshold colour value:
  - using the change in colour value of the sorbent material from the initial time point to the final time point; and
- when the change in colour value of the sorbent material from the initial time point to the final time point is greater than or equal to the threshold colour value:
  - using a rate of change in colour value of the sorbent material over a time range, wherein the time range is between the initial time point and the final time point.

The colour value may be an absorbance. In the case where the colour value is an absorbance, it may be the absorbance of the halochromic indicator sorbed on and/or in the sorbent material. In this instance, a change in the absorption spectrum of the indicator may comprise a change in wavelength. It may comprise a change in intensity. The change in the absorption spectrum may be substantially independent of the volume of the fluid exposed to the sorbent material. It may be substantially independent of the flow rate of the fluid exposed to the sorbent material.

The colour value may be a wavelength. In the case where the colour value is a wavelength, it may be the wavelength of maximum absorbance of the halochromic indicator sorbed on and/or in the sorbent material. A change in wavelength of the absorption maximum of the indicator may also comprise a change in intensity of the absorption maximum of the indicator. The change in the absorption spectrum of the indicator may comprise a change in intensity of the absorption of the indicator at a particular wavelength or at more than one wavelength. It may be a change in colour, or a change in absorption e.g. absorbance of electromagnetic radiation. The electromagnetic radiation may be, for example, infrared, far infrared, near infrared, visible, ultraviolet, or some other electromagnetic radiation.

The absorption spectrum of the halochromic indicator may vary monotonically over an operational pH range. The halochromic indicator may be selected from the group consisting of methyl orange, methyl red, methyl yellow chlorophenol red, bromocresol green, congo red, thymol blue, bromophenol blue, cresol red, metacresol purple, malachite green, ethyl violet, crystal violet, 2,4-dinitrophenol, orange IV, erythrosin B, p-(phenylazo)diphenylamine, p-phenylazoaniline, phenol blue, and mixtures thereof. It may, for example, be selected from the group consisting of thymol blue, bromophenol blue, and mixtures thereof. In certain embodiments, the halochromic indicator is bromophenol blue.

In the case where the change in absorption spectrum of the indicator is a change in intensity at a particular wavelength or wavelengths, each particular wavelength or wavelengths may be within the range of from about 10 nm to about 300 μm, or from about 390 nm to about 700 nm, about 10 nm to about 400 nm, about 700 nm to about 300 μm, about 390 nm to about 500 nm, about 500 nm to about 600 nm, or about 600 nm to about 700 nm. It may be, for example, at about 10 nm, 50 nm, 100 nm, 200 nm, 300 nm, 400 nm, 425 nm, 450 nm, 475 nm, 500 nm, 525 nm, 550 nm, 575 nm, 600 nm, 625 nm, 650 nm, 675 nm, 700 nm, 800 nm, 900 nm, 1 μm, 2 μm, 5 μm, 10 μm, 20 μm, 50 μm, 100 μm, 200 μm, or 300 μm.

In the case where the change in the absorption spectrum of the indicator is a change in wavelength of the absorption maximum of the indicator, the absorption maximum may mean the maximum absorption in a particular region of the electromagnetic spectrum. It may mean, for example, the maximum absorption in a region of from about 10 nm to about 300 μm, or from about 390 nm to about 700 nm, about 10 nm to about 400 nm, about 700 nm to about 300 μm, about 390 nm to about 500 nm, about 500 nm to about 600 nm, or about 600 nm to about 700 nm.

In certain embodiments, when the change in colour value of the sorbent material from the initial time point to the final time point is smaller than the threshold colour value, the concentration of analyte is calculated using the equation:

$$AC=M_{CC}*CC+ACI_1$$

wherein AC is the analyte concentration; CC is the change in colour value of the sorbent material from the initial time point to the final time point; and $M_{CC}$ is a slope and $ACI_1$ is a y-intercept, respectively, of a standard plot of colour change value of the sorbent material versus analyte concentration.

In certain embodiments, when the change in colour value of the sorbent material from the initial time point to the final time point is greater than or equal to the threshold colour value, the concentration of analyte is calculated using the equation:

$$AC=M_{CCR}*CCR+ACI_2$$

wherein AC is the analyte concentration; CCR is the rate of change in colour value of the sorbent material over the time range; and $M_{CCR}$ is a slope and $ACI_2$ is a y-intercept, respectively, of a standard plot of rate of colour change value of the sorbent material versus analyte concentration.

The method may be capable of rapidly determining the concentration of the analyte in the fluid. It may, for example, be capable of determining the concentration of the analyte in the fluid in less than about 10 minutes, or less than about 5 minutes, 2 minutes, 1 minute, 45 seconds or 30 seconds after exposure of the fluid to the sorbent material.

In some instances, the method does not comprise a titration step. In the case where the method does not comprise a titration step, the method may require only a small liquid volume, such as less than 1 mL. This may enable the method to be integrated into a simplified device design when compared with devices requiring a titration step, and/or may enable the device to be portable. In such a case, the method may be simple to use. That is, it may not require a highly skilled operator. It may, for example, be suitable for an unskilled operator to use.

In certain embodiments, the initial and final colour change values of the sorbent material may be measured using a photosensor.

In certain specific embodiments, the method comprises:

- collecting a fluid sample from a subject in a vessel;
- exposing the sorbent material to a light;
- measuring the initial colour value of the sorbent material at the initial time point;
- pumping the fluid through a filter to the sorbent material at a constant flow rate;
- measuring a second colour value of the sorbent material at a second time point, the second time point being at a time after the initial time point;
- measuring a third colour value of the sorbent material at a third time point, the third time point being at a time after the second time point and before the final time point;
- ceasing the pumping; and
- measuring the final colour value of the sorbent material at the final time point.

The method may use the system described herein. The system described herein may be used in the method.

Threshold Colour Value

The threshold colour value may be a colour value corresponding to a concentration of analyte of from about 50 ppm to about 1000 ppm (v/v) in the fluid, or from about 100 ppm to about 1000 ppm, about 200 ppm to about 1000 ppm, about 300 ppm to about 1000 ppm, about 50 ppm to about 800 ppm, about 50 ppm to about 700 ppm, about 50 ppm to about 500 ppm, about 200 ppm to about 800 ppm, about 250 ppm to about 500 ppm, or about 300 ppm to about 400 ppm (v/v) in the fluid.

Sorbent Material

The sorbent material may be transparent or at least partially transparent. It may be opaque. The sorbent material may be disposed within a flow channel, or an analysis chamber. It may be disposed on or in a test strip. It may be a component of a test strip.

The sorbent material may be a surface. It may be a glass surface. It may be a polymer surface. It may be a surface-modified material, for example a surface modified glass. It may be a liquid vessel, sponge, hydrogel, paper, or an absorbent polymer. The sorbent material may comprise a polymer fibre. It may be a porous material, such as paper. It may comprise a wettable polymer. It may comprise cellulose, nitrocellulose, polypropylene or a combination thereof. It may comprise a hydrophilic region and/or a hydrophobic region. The hydrophilic region may comprise a wettable material. It may be a porous material. The hydrophobic region may comprise a hydrophobic polymer, a wax, or a combination thereof. The sorbent material may be disposed on an at least partially optically transparent substrate. It may be disposed on an optically opaque substrate. In certain embodiments, the sorbent material is cellulose, optionally natural cellulose.

The sorbent material may further comprise a weak base sorbed thereon and/or therein. The weak base may be, for example, selected from the group consisting of bicarbonate salts, ammonia, aniline, phenolate salts, and mixtures thereof. It may be, for example, a bicarbonate salt. It may be sodium bicarbonate. The weak base may be used to adjust the working range of the device by increasing the pH at a surface of the sorbent material. The weak base may have a pKb of greater than about 3, or greater than about 4, 5, 6, 7, 8, 9, or 10. The weak base may have a pKb of from about 3 to about 12, or from about 3 to about 10, about 3 to about 8, about 5 to about 12, about 5 to about 10, about 6 to about 9, or about 7 to about 8. It may be, for example, about 3, 3.5, 4, 4.5, 5, 5.5, 6, 6.5, 7, 7.2, 7.4, 7.6, 7.8, 8, 8.2, 8.4, 8.6, 8.8, 9, 9.5, 10, 10.5, 11, 11.5, or 12.

Hydroxylammonium Salt

The optionally hydroxylammonium salt may be selected from the group consisting of hydroxylammonium chloride, hydroxylammonium sulfate, hydroxylammonium phosphate, hydroxylammonium nitrate, and mixtures thereof. In certain embodiments it may be hydroxylammonium chloride.

Halochromic Indicator

The halochromic indicator may be an indicator which changes absorption spectrum as a result of a change in pH of the liquid. The halochromic indicator may comprise more than one indicator. It may comprise a plurality of indicators, each indicator having a transition pH range, whereby the transition pH ranges of the plurality of indicators together span the operational pH range of the liquid. It may, for example, be selected from the group consisting of methyl orange, methyl red, methyl yellow chlorophenol red, bromocresol green, congo red, thymol blue, bromophenol blue, cresol red, metacresol purple, malachite green, ethyl violet, crystal violet, 2,4-dinitrophenol, orange IV, erythrosin B, p-(phenylazo)diphenylamine, p-phenylazoaniline, phenol blue, and mixtures thereof. It may, for example, be selected from the group consisting of thymol blue, bromophenol blue, and mixtures thereof. In certain embodiments, the halochromic indicator is bromophenol blue.

The absorption spectrum of the halochromic indicator may vary monotonically over an operational pH range. The term "operational pH range" may mean the pH range of the sorbent material from the pH if the sorbent material was not exposed to any analyte, to the pH if the sorbent material was exposed to pure undiluted analyte for sufficient time for the pH to reach a steady state. The term "transition pH range" means the pH range in which small changes in pH produce a change in the indicator maximum absorption. The operational pH range of the halochromic indicator may be from about 1 to about 9, about 1 to about 8, about 1 to about 7, about 1 to about 6, about 1 to about 5, about 2 to about 7, about 3 to about 7, about 4 to about 7, about 2 to about 5, or about 2 to about 4.

The halochromic indicator may be selected to have an operational pH range that includes a pH range below the pH of the liquid prior to exposure of the sorbent material to a concentration of the analyte in a fluid. It may be selected to have an operational pH range that includes a pH range below the pH of the fluid prior to exposure of the hydroxylammonium salt to a concentration of the analyte (i.e. the acetone) in a fluid. The halochromic indicator may change from a neutral species at a higher pH to a charged species at a lower pH.

The change in the absorption spectrum of the halochromic indicator may be a change of absorption maximum of the halochromic indicator. In this case, the change in the absorption maximum of the halochromic indicator may comprise a change in wavelength of the absorption maximum of the halochromic indicator. It may comprise a change in intensity of the absorption maximum of the halochromic indicator. It may comprise a change in wavelength and intensity. The change in the absorption spectrum of the halochromic indicator may comprise a change in intensity of the absorption of the halochromic indicator at a particular wavelength or at more than one wavelength. It may be a change in colour, or a change in absorption e.g. absorbance of electromagnetic radiation. The electromagnetic radiation may be, for example, infrared, far infrared, near infrared, visible, ultraviolet, or some other electromagnetic radiation.

In the case where the change in absorption spectrum of the halochromic indicator is a change in intensity at a particular wavelength or wavelengths, each particular wavelength or wavelengths may be within the range of from about 10 nm to about 300 μm, or from about 390 nm to about 700 nm, about 10 nm to about 400 nm, about 700 nm to about 300 μm, about 390 nm to about 500 nm, about 500 nm to about 600 nm, or about 600 nm to about 700 nm. It may be, for example, at about 10 nm, 50 nm, 100 nm, 200 nm, 300 nm, 400 nm, 425 nm, 450 nm, 475 nm, 500 nm, 525 nm, 550 nm, 575 nm, 600 nm, 625 nm, 650 nm, 675 nm, 700 nm, 800 nm, 900 nm, 1 μm, 2 μm, 5 μm, 10 μm, 20 μm, 50 μm, 100 μm, 200 μm, or 300 μm.

In the case where the change in the absorption spectrum of the halochromic indicator is a change in wavelength of the absorption maximum of the halochromic indicator, the absorption maximum may mean the maximum absorption in a particular region of the electromagnetic spectrum. It may mean, for example, the maximum absorption in a region of from about 10 nm to about 300 μm, or from about 390 nm to about 700 nm, about 10 nm to about 400 nm, about 700 nm to about 300 μm, about 390 nm to about 500 nm, about 500 nm to about 600 nm, or about 600 nm to about 700 nm.

Fluid

The fluid may be a gas, liquid, vapour or combination thereof. It may be a dispersion. It may be an emulsion. It may be a microemulsion. It may be a sol. It may be a solution, for example an aqueous or organic solution. It may be a suspension. It may be a biological fluid. It may be, for example, whole blood, breath, sweat, sputum, mucus, urine, serum, semen, plasma, or saliva. The fluid may be derived from a solid, for example by dissolution of the solid in a solvent. In certain embodiments, the fluid is breath.

Analyte

The analyte may be a metal, non-metal, cation, anion, radioisotope, organic or non-organic chemical. It may be a biomarker for diet, a disease, or a disorder. It may be a metal, protein, antibody, or small organic molecule. The analyte may be, for example, a ketone, such as acetone. The analyte may be a carbonyl-containing compound. It may, for example, be acetone.

The analyte may be a carbonyl-containing compound. The carbonyl-containing compound may be selected from the group consisting of ketones, aldehydes, esters, thioesters, amides, and carboxylic acids. It may be a biomarker for diet, a disease, or a disorder. It may be a protein, antibody, or small organic molecule. It may, for example, be selected from the group consisting of acetoacetate, butyraldehyde, 4-hydroxy-2-hexenal, ethyl acetate, acetic acid, 4-hydroxy-2-nonenal, 2-pentanone, 2-butanone, 3-hydroxy-2-butanone, hydroxyacetaldehyde, acetaldehyde, pentanal, malondialdehyde, acrolein, beta-hydroxybutyrate, and acetone. It may, for example, be acetone.

Liquid

The liquid may be water, or some other suitable solvent. It may be an organic solvent, an aqueous solution, or a combination thereof. It may be suitable for dissolving the hydroxylammonium salt. It may be suitable for dissolving the analyte (e.g. acetone). The liquid, or a portion thereof, may be a component of the fluid. Alternatively, or additionally, the liquid, or a portion thereof, may be separate to the fluid. In the case where the liquid is separate to the fluid, the liquid may be added to the hydroxylammonium salt prior to or during exposure of the fluid to the hydroxylammonium salt. The liquid may, for example, be pre-sorbed onto the sorbent material. The hydroxylammonium salt may be in a solution with the liquid prior to exposure to the fluid. In certain embodiments, the liquid is delivered by a build-in liquid delivery device in the system.

The liquid volume may be about 1 mL or less. It may be less than about 0.5 mL, 0.2 mL, 0.1 mL, 0.05 mL, 0.02 mL, or 0.01 mL. The liquid volume may be from about 0.001 mL to about 1 mL, or from about 0.001 mL to about 0.5 mL, about 0.001 mL to about 0.2 mL, about 0.005 mL to about 0.5 mL, about 0.005 mL to about 0.05 mL, or about 0.005 mL to about 1 mL.

Photosensor

The photosensor may be sensitive to a defined range of electromagnetic radiation, for example, ultraviolet-A (UVA), ultraviolet-B (UVB), ultraviolet-C (UVC), visible light, near-infrared (NIR), far-infrared (FIR), or some combination thereof. It may be a change-coupled device (CCD), an active pixel sensor, or a hybrid thereof. It may, for example, be a complementary metal-oxide-semiconductor (CMOS) sensor, or a scientific complementary metal-oxide-semiconductor (sCMOS) sensor. The skilled person will understand that various sensing apparatuses can be used as the photosensor such as, for example, a red-green-blue (RGB) colour sensor, a photodiode, a photoresistor, a phototransistor, a photovoltaic cell, or an image sensor used, for example, in a smart phone. The photosensor may comprise a camera and a light source. It may comprise a smart phone. The system may comprise one or more filters, optionally optical filters, which selectively allow particular wavelengths or combinations of wavelengths of electromagnetic radiation to reach the photosensor.

In certain embodiments, the photosensor is capable of measuring three bands of visible light: long wavelengths, peaking near 564-620 nm (red); medium-wavelength, peaking near 534-560 nm (green); and short-wavelength light, peaking near 420-440 nm (blue). In certain embodiments, the photosensor utilises a particular visible light band for its measurement based on the type of halochromic indicator used.

The photosensor may be configured to measure a response (i.e. the colour value of the sorbent material) of the system as a function of time. It may be configured to measure the change in the colour value of the sorbent material at one or more defined or predetermined times after exposure of the hydroxylammonium salt to the analyte. The times may be, for example, from about 0.01 seconds to about 120 seconds, or it may be from about 0.01 seconds to about 60 second, or about 0.01 seconds to about 30 seconds. It may be less than about 120 seconds, or less than about 60, 30, or 20 seconds. It may be, for example, about 0.01, 0.02, 0.05, 0.1, 0.2, 0.5, 1, 2, 5, 10, 15, 20, 25, 30, 35, 40, 45, 50, 55, 60, 70, 80, 90, 100, 110, or 120 seconds after exposure of the hydroxylammonium salt to the analyte.

System

Disclosed herein is a system for determining a concentration of an analyte in a fluid, said system comprising: a vessel receiving unit, capable of receiving a fluid sample vessel; a sorbent material having a hydroxylamine salt and a halochromic indicator sorbed thereon and/or therein; a pump for pumping a fluid from the fluid sample vessel to the sorbent material; a light emitting unit for exposing the sorbent material to a light; a photosensor for measuring a colour value of the sorbent material at an initial time point and a final time point; and a control unit, configured to determine the concentration of analyte in the fluid by:

- when a change in colour value of the sorbent material from the initial time point to the final time point is smaller than a threshold colour value:
  - using the change in colour value of the sorbent material from the initial time point to the final time point; and
- when the change in colour value of the sorbent material from the initial time point to the final time point is greater than or equal to the threshold colour value:
  - using a rate of change in colour value of the sorbent material over a time range, wherein the time range is between the initial time point and the final time point.

The pump may be capable of pumping the fluid from the fluid sample vessel to the sorbent material at a constant flow rate.

The system may further comprise a filter for removing moisture from the fluid.

The colour value may be an absorbance. It may be a wavelength. The colour value may be substantially as described hereinbefore in relation to the method.

The hydroxylammonium salt may be substantially as hereinbefore described in relation to the method. For example, the hydroxylammonium salt may be hydroxylammonium chloride.

The halochromic indicator may be substantially as hereinbefore described in relation to the method. For example, in certain embodiments the halochromic indicator may be selected from the group consisting of methyl orange, methyl red, methyl yellow, methyl green, methyl violet, chlorophenol red, bromocresol green, conga red, thymol blue, bromophenol blue, cresol red, metacresol purple, malachite green, ethyl violet, crystal violet, 2,4-dinitrophenol, orange IV, erythrosin B, p-(phenylazo)diphenylamine, p-phenylazoaniline and mixtures thereof. In certain embodiments, the halochromic indicator is bromophenol blue.

The fluid may be substantially as hereinbefore described in relation to the method. For example, in certain embodiments the fluid may be breath.

The sorbent material and liquid may be substantially as hereinbefore described in relation to the method.

The photosensor may be substantially as hereinbefore described in relation to the method.

The system may be portable. It may be non-portable. It may be a detector. It may be a handheld system, for example a handheld detector. The sorbent material may be removably disposed within the system. The system may be a reusable device. It may be portable. It may be non-portable. It may be integrated within a portable health monitoring device. It may be suitable for determining a concentration of an analyte, e.g., acetone in a fluid, for example, a liquid, vapour, gas or mixture thereof. The system may comprise a strip. It may be a lab-on chip.

The skilled person will understand that the system may be any suitable shape or size. It may comprise an inlet for passing the fluid through. In the case where the fluid is breath, the system may comprise a mouthpiece for breathing through. The system may be connected to a larger system that utilises analytical methods such as machine learning and neural networking to provide both historical and predictive analysis of a user's carbonyl-containing compound levels. The system may be attachable, or connectable to a smartphone. It may comprise a smartphone. The system may be suitable for an unskilled operator to use. That is, it may be simple to use, such that a person without any formal training may be able to use the device by, for example, following a set of oral, written, and/or pictorial instructions.

The system may further comprise a flow channel or an analysis chamber. The sensor may be disposed within the flow channel or analysis chamber. It may be located so as to be exposed to fluid in the flow channel or analysis chamber. It may, for example, form part of an inner surface or wall of the flow channel or analysis chamber. The system may further comprise a flow controller configured to control and/or monitor a flow rate of the fluid into the analysis chamber or through the flow channel. It may comprise a volume controller configured to control and/or monitor the volume of the fluid passing into the analysis chamber or through the flow channel.

The system may be selective for the analyte (e.g. acetone). It may respond to the analyte but not substantially respond to any other component of the fluid at a position of the sensor. It may produce a higher response to the analyte when compared with its response to a non-analyte component of the fluid at the same concentration at a position of the sensor. It may produce a faster response to the analyte when compared with its response to a non-analyte component of the fluid at the same concentration at a position of the sensor. The ratio of the system response to the analyte, to the system response to any particular non-analyte (e.g. non-acetone) component of the fluid at the same concentration may be from about 1.5 to about $1\times10^6$, or it may be from about 2 to about $1\times10^6$, about 5 to about $1\times10^6$, about 10 to about $1\times10^6$, about 50 to about $1\times10^6$, about 100 to about $1\times10^6$, or about $1\times10^3$ to about $1\times10^6$. It may be greater than about 1.5, 2, 5, 10, 20, 50, 100, 200, 500, 1000, or $1\times10^4$.

The system may be sensitive to the analyte (e.g. acetone). It may have a limit of detection (LOD) for the analyte of less than about 1000 ppm, or less than about 500 ppm, 200 ppm, 100 ppm, 50 ppm, 20 ppm, 10 ppm, 5 ppm, 2 ppm, 1 ppm, 500 ppb, 200 ppb, 100 ppb, 50 ppb, 10 ppb, 5 ppb, 2 ppb, or 1 ppb. It may have a LOD for the analyte of from about 0.1 ppb to about 1000 ppm, or from about 5 ppb to about 500 ppm, about 10 ppb to about 500 ppm, about 10 ppb to about 1000 ppm, about 100 ppb to about 500 ppm, about 500 ppb to about 500 ppm, or about 1 ppm to about 500 ppm. It may have a limit of quantitation (LOQ) for the analyte of less than about 1000 ppm, or less than about 500 ppm, 200 ppm, 100 ppm, 50 ppm, 20 ppm, 10 ppm, 5 ppm, 2 ppm, 1 ppm, 500 ppb, 200 ppb, 100 ppb, 50 ppb, 10 ppb, 5 ppb, 2 ppb, or 1 ppb. It may have a LOQ for the analyte of from about 0.1 ppb to about 1000 ppm, or from about 5 ppb to about 500 ppm, about 10 ppb to about 500 ppm, about 100 ppb to about 500 ppm, about 500 ppb to about 500 ppm, or about 1 ppm to about 500 ppm.

The dynamic range of the system may be from about 0.1 ppb to about 1000 g/L, or from about 5 ppb to about 1000 g/L, about 10 ppb to about 1000 g/L, about 10 ppb to about 1000 ppm, about 100 ppb to about 1000 g/L, about 500 ppb to about 1000 g/L, about 1 ppm to about 1000 g/L, about 10 ppm to about 1000 g/L, about 100 ppm to about 1000 g/L, or about 1000 ppm to about 1000 g/L.

The working range of the system may be from about 0.1 ppb to about 1000 g/L, or from about 5 ppb to about 1000 g/L, about 10 ppb to about 1000 g/L, about 100 ppb to about 1000 g/L, about 500 ppb to about 1000 g/L, about 1 ppm to about 1000 g/L, about 10 ppm to about 1000 g/L, about 100 ppm to about 1000 g/L, or about 1000 ppm to about 1000 g/L.

The accuracy of the system may be such that its percentage relative error for the analyte (e.g. acetone) may be less than about 30%, or less than about 20%, 10%, 5%, 2%, 1%, 0.5%, 0.2%, 0.1%, 0.05%, 0.02%, or 0.01%.

The precision of the system may be such that its percentage relative standard deviation for an analyte (e.g. acetone) concentration may be less than about 30%, or less than about 20%, 10%, 5%, 2%, 1%, 0.5%, 0.2%, 0.1%, 0.05%, 0.02%, or 0.01%.

The system may further comprise a neutralisation chamber, said neutralisation chamber comprising a neutralisation reagent capable of neutralising a compound, such as the hydroxylammonium salt, or a product of the reaction between the analyte and the hydroxylammonium salt. In this context, "neutralisation" indicates that the compound is converted to a less hazardous and/or more environmentally friendly product or products. The neutralisation reagent may comprise a biological and/or a chemical material. It may comprise a bacterium. It may, for example, comprise a bacterium selected from the *Nitrosomonas* genus. It may, for example, comprise *Nitrosomonas europaea*. It may comprise an enzyme. It may comprise an oxidant. It may comprise, for example, one or more compound selected from the group consisting of hydrogen peroxide, chlorite salts, chlorate salts, perchlorate salts, hypochlorite salts, and mixtures thereof. The neutralisation reagent may be able to react with the hydroxylammonium salt. It may be able, for example, to oxidise the hydroxylammonium salt.

This may serve to convert the hydroxylammonium salt into a less hazardous and/or more environmentally friendly product or products, such as ammonia, water and dilute nitric acid.

Control Unit

The control unit may be configured to calculate the concentration of the analyte in the fluid from the change in colour value of the sorbent material. It may be configured to determine the concentration of the analyte in the fluid by:

- when a change in colour value of the sorbent material from the initial time point to the final time point is smaller than a threshold colour value:
  - using the change in colour value of the sorbent material from the initial time point to the final time point; and
- when the change in colour value of the sorbent material from the initial time point to the final time point is greater than or equal to the threshold colour value:
  - using a rate of change in colour value of the sorbent material over a time range, wherein the time range is between the initial time point and the final time point.

The control unit may be configured to determine the concentration of analyte in the fluid by comparing the change in colour value of the sorbent material to a standard curve. In this example, the standard curve may be a plot of the colour value of the sorbent material for a variety of known analyte concentrations. Alternatively, or additionally, the standard curve may be a plot of the rate of change of colour value of the sorbent material for a variety of known analyte concentrations. The standard curve may, for example, be expressed as a mathematical function. It may, for example, express the concentration of the analyte in the fluid as a function of the change in colour value of the sorbent material. In this case the control unit may use the function to calculate the concentration of the analyte from the change in colour value measured by the photosensor. Alternatively, or additionally, the standard curve may be expressed as a mathematical function that expresses the concentration of the analyte in the fluid as a function of the rate of change in colour value of the sorbent material.

The control unit may be configured to calculate the concentration of analyte in the fluid using the response at one or more exposure regions of the sorbent layer, optionally 2, 3, 4, 5, 10, 50, 100 or more than 100 exposure regions thereof.

Method of Managing Diabetes

Disclosed herein is a method of managing diabetes in a patient on a diabetes treatment plan. The method comprises determining an acetone concentration of a breath sample of the patient using the method of determining a concentration of acetone in a fluid as described above; comparing the acetone concentration to a reference acetone concentration range; and if the acetone concentration is outside the acetone concentration reference range, adjusting the diabetes treatment plan.

The diabetes treatment plan may be adjusted, for example, by modifying the administration timing or dosage of a blood glucose management medication. It may be adjusted, for example, by an administration of insulin, or modification of the patient's total daily dose of insulin. It may be adjusted by modifying the fluid and/or nutrient intake of the patient. It may be adjusted by an administration of glucagon. It may be adjusted, for example, by initiating immediate medical attention, in particular in the case of ketoacidosis.

The method may use the system disclosed herein. The system disclosed herein may be used in the method.

EXAMPLES

The present invention will now be further described in greater detail with reference to the following specific examples, which should not be construed as in any way limiting the scope of the invention.

Example 1: A System and Method for the Measurement of Breath Acetone

In the following example, the developed reagent contains hydroxylamine hydrochloride ($NH_3OH{\cdot}HCl$), which reacts with acetone ($(CH_3)_2CO$) to form acetone oxime ($(CH_3)_2CNOH$), hydrochloric acid (HCl) and water ($H_2O$) as indicated in Formula (1).

$$(CH_3)_2CO+NH_3OH{\cdot}HCl \rightarrow (CH_3)_2CNOH+HCl+H_2O \quad (1)$$

The amount of hydrochloric acid formed depends on the concentration of the acetone and the amount of gas sample. By keeping a constant amount of gas sample, the acidity of the reagent changes with the acetone concentration. By adding a pH indicator into the reagent, the change of acidity of the reagent can be revealed by observing a colour change of the reagent.

There is provided a system 100 that determines the concentration of acetone in an exhaled breath sample by measuring the colour change of the reagent sorbed in and/or on a sorbent material. The system is configured as shown in FIG. 1. The air bottle 110 collects exhaled gas 101 from the breath of a human subject. The gas path 105 is depicted using bold arrows. An air filter 115 removes moisture from the gas sample when the gas sample is pumped using pump 120 to the sorbent material testing strip 125 for reaction with the hydroxylammonium salt and halochromic indicator reagents sorbed on and/or in the sorbent material. The pump 120 pumps the gas sample to the testing strip at a constant flow rate to control the amount of gas sample reacting with the reagents. A light emitting unit 130 and photo sensor 150 measure the colour change of the reagents sorbed on and/or in the sorbent material 125. The light path is shown as 145. The system is powered by a battery 155 for portable application. There are control buttons 160 and a display unit 165 as the user-machine interface. The whole system is controlled by the firmware programmed in a main control unit 140. Wire connections are shown as 135. The acetone concentration is calculated by a method programmed in firmware in the main control unit as described in detail below.

Figure 2:
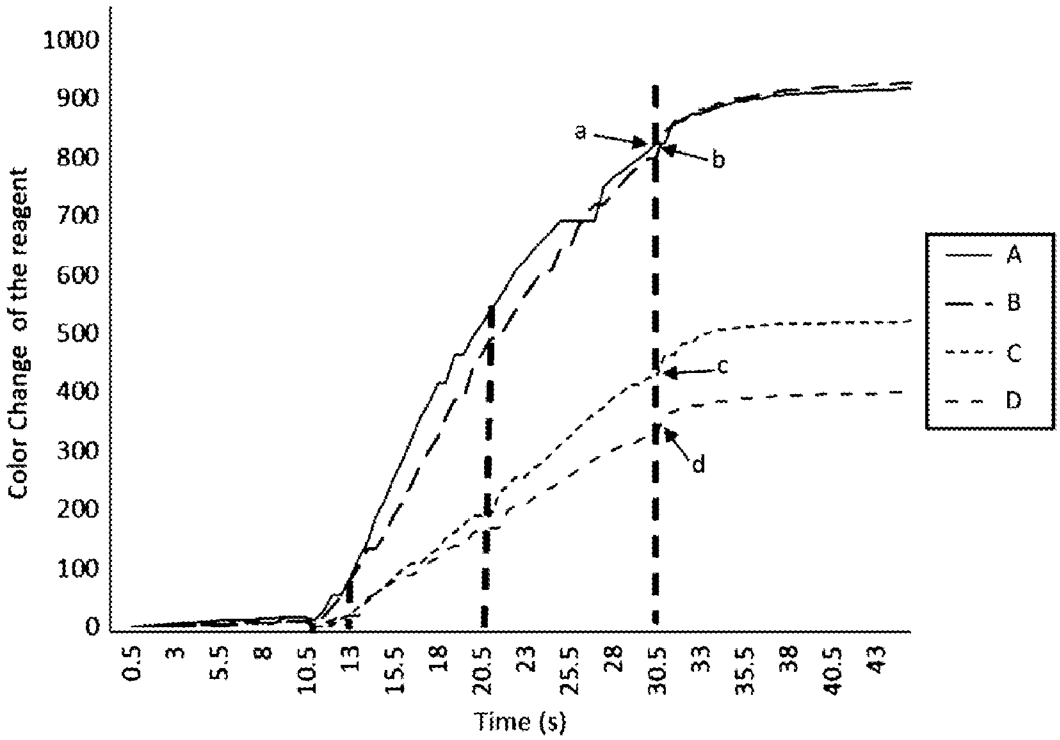
FIG. 2: Typical colour change profiles of an example system according to a specific embodiment of the invention for acetone concentrations of (A) 400 ppm, (B) 300 ppm, (C) 100 ppm, and (D) 80 ppm.

The total volume of the gas sample interacting with the reagent is maintained constant by pumping the gas sample into the testing strip at a constant flow rate for a predefined duration. When the hydroxylamine hydrochloride sorbed in and/or on the sorbent material is not fully reacted with the acetone, the colour of the sorbent material will change with the concentration of the acetone in the gas sample. However, when the concentration of the acetone is high, the colour change of the sorbent material will be saturated at a particular value. As illustrated in FIG. 2, the colour changes between time at 10.5 second and time at 30.5 second for acetone concentrations of 80 parts per million (ppm) (D) and 100 ppm (E) are $CC_{80\ ppm}$ (d) and $CC_{100\ ppm}$ (e) respectively. For these acetone concentrations the change of colour varies with the concentration of the acetone. However, the changes of colour of the sorbent material are saturated at the acetone concentrations of 300 ppm (B) and 400 ppm (A), shown as $CC_{300\ ppm}$ (b) and $CC_{400\ ppm}$ (a) in FIG. 2. Thus, when the acetone concentration is in the low range, the acetone concentration can be determined by observing the colour change of the reagent. However, when the acetone concentration is in the high range, the acetone concentration can be determined by observing the rate of colour change of the reagent, instead of the colour change per se.

Figure 3:
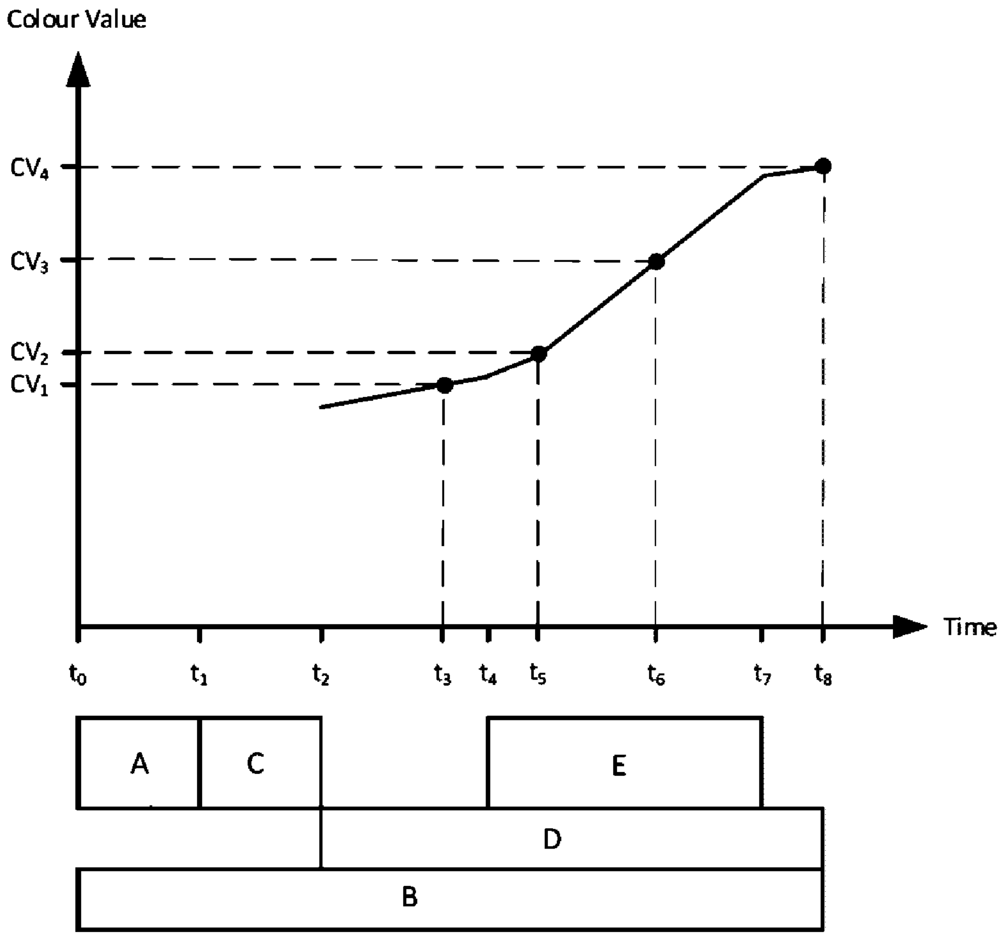
FIG. 3: Schematic diagram of the operation of an example system during a measurement process.

Also disclosed is a method to calculate the acetone concentration by observing both colour change and rate of colour change of the reagent. The method is programmed into the firmware of the system and operates as indicated in FIG. 3.

At time to, the light emitting unit will be powered on (step B) and the user will be prompted to insert the testing strip (step A). At time $t_1$, the user will be prompted to insert the air bottle (step C). At time $t_2$, the system will power on the photo sensor (step D). At time $t_3$, the system will read colour value, $CV_1$. At time $t_4$, the system will power-on the pump (step E). At time $t_5$, the system will read colour value, $CV_2$. At time $t_6$, the system will read colour value $CV_3$. At time $t_7$, the system will power-off the pump. At time $t_8$, the system will read colour value $CV_4$.

Figure 4:
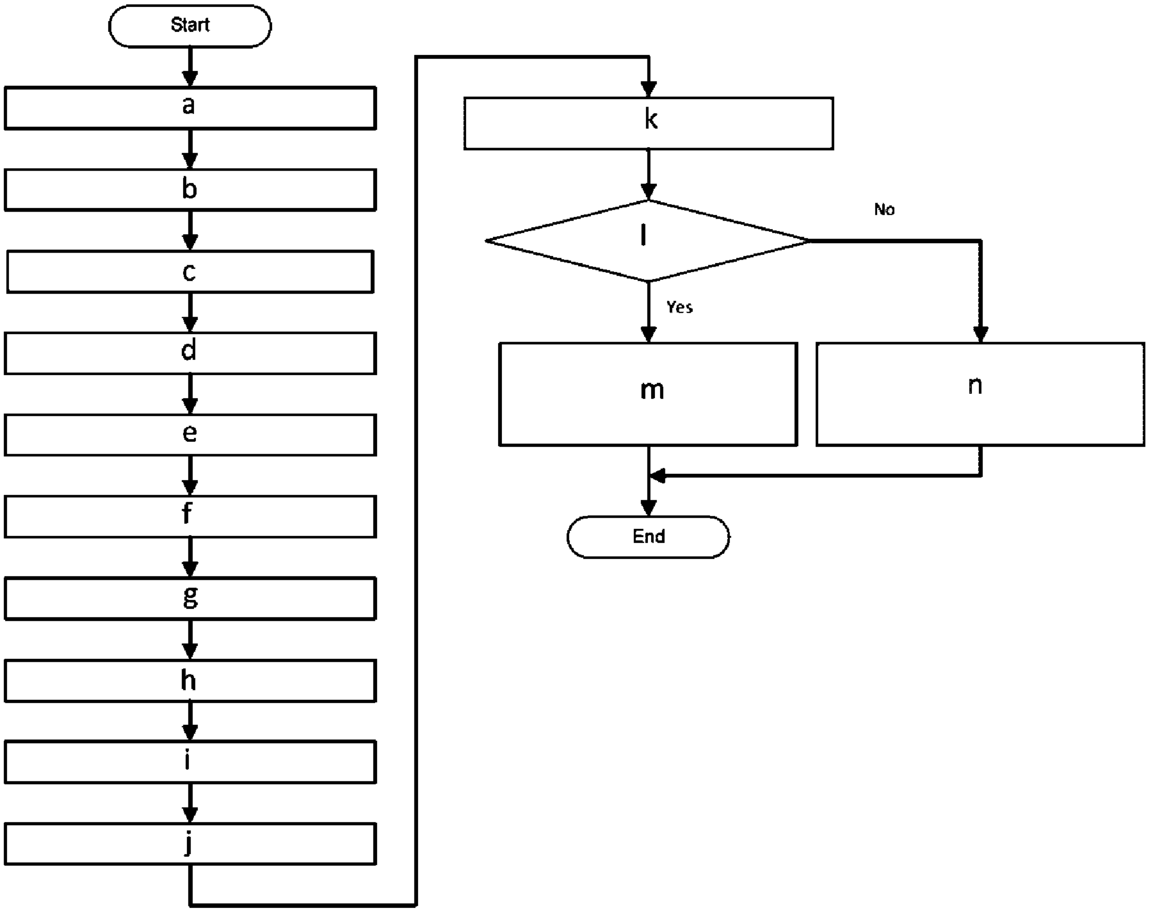
FIG. 4: Flowchart of the firmware of an example system.

FIG. 4 shows a flowchart of the firmware for the control unit 140, which at time to, powers on the light emitting unit (a) and prompts the user to insert the testing strip (b). At time $t_1$, the user will be prompted to insert the air bottle (c). At time $t_2$, the system will power on the photo sensor (d). At time $t_3$, it will read colour value, $CV_1$ (e). At time $t_4$, it will power-on the pump (f). At time $t_5$, it will read colour value, $CV_2$ (g). At time $t_6$, it will read colour value $CV_3$ (h). At time $t_7$, it will power-off the pump (i). At time $t_8$, it will read colour value $CV_4$ (j). Then, the system will calculate the colour change (k) with Formula (2).

$$CC=(CV_4-CV_1) \quad (2)$$

Figure 5:
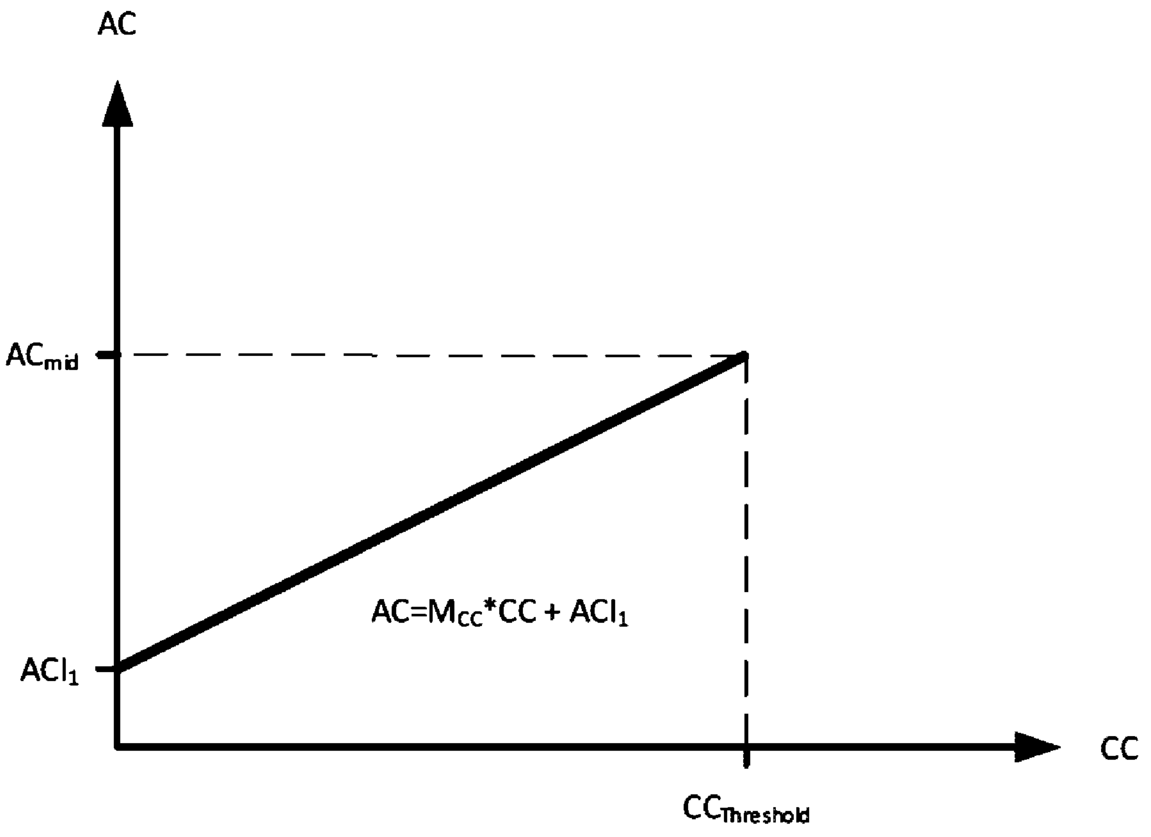
FIG. 5: Illustration of a formula used for calculating the acetone concentration according to an example inventive method.

The system will next assess whether the calculated colour change (CC) is smaller than a threshold colour change value ($CC_{Threshold}$) (l). If the CC is less than $CC_{Threshold}$, the system will calculate the analyte (e.g. acetone) concentration using the Formulas (3)-(4) (m), where $AC_{mid}$, $AC_{min}$, $CC_{max}$, $CC_{min}$ and $ACI_1$ are pre-defined parameters obtained by clinical trial. AC mid being the middle (e.g. threshold) of the acetone concentration, which is the boundary between a low range (e.g. 0-50 ppm) to high range of acetone measurements (e.g. 50-500 ppm). $AC_{min}$ is the minimum value of the acetone measurement range. $CC_{max}$ means the maximum change of colour value. $CC_{min}$ is the minimum change of colour value. $ACI_1$ is the y-intercept in a linear equation of the acetone concentration versus the change in colour value. FIG. 5 illustrates Formula (4).

$$MCC=(AC_{mid}-AC_{min})/(CC_{max}-CC_{min}) \quad (3)$$

$$AC=M_{CC}*CC+ACI_1 \quad (4)$$

Figure 6:
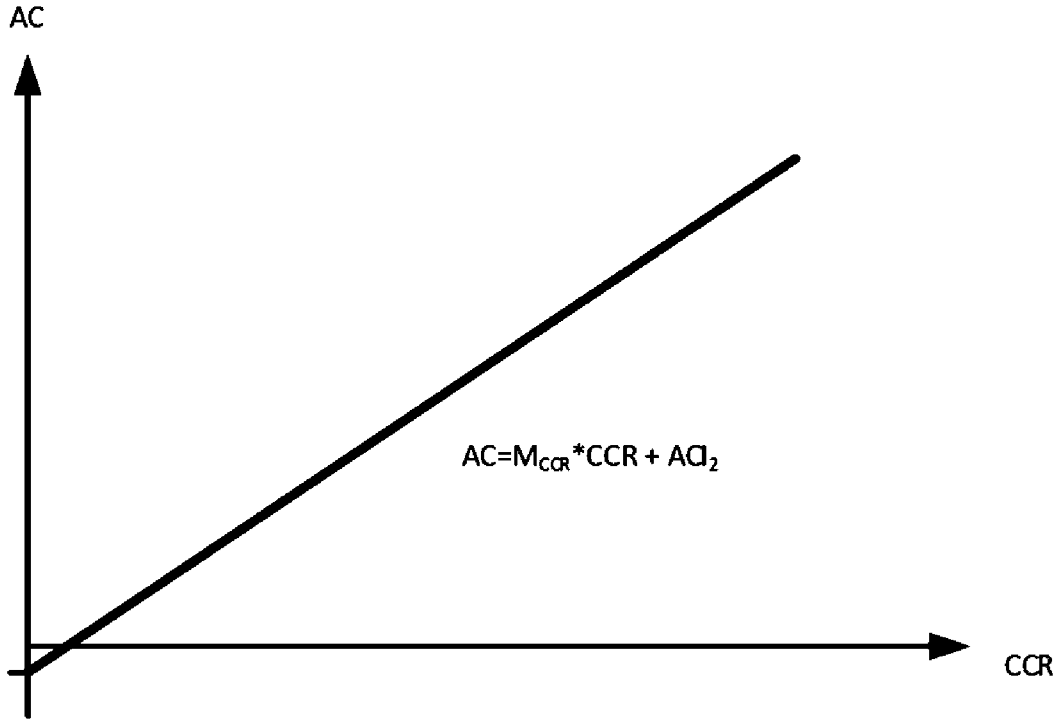
FIG. 6: Illustration of a formula used for calculating the acetone concentration according to an example inventive method.

When the calculated CC is equal or larger than $CC_{Threshold}$, the system will calculate the colour change rate (CCR) using Formula (5) and will calculate the analyte (e.g. acetone) concentration using Formulas (6)-(7) (n), where $AC_{max}$, $AC_{mid}$, $CCR_{max}$, $CCR_{min}$ and $ACI_2$ are pre-defined parameters obtained by clinical trial. AC mid being the middle (e.g. threshold) of the acetone concentration, which is the boundary between a low range (e.g. 0-50 ppm) to high range of acetone measurements (e.g. 50-500 ppm). $AC_{max}$ is the maximum value of the acetone measurement range. $CCR_{max}$ means the maximum rate of change of colour value. $CCR_{min}$ is the minimum rate of change of colour value. $ACI_2$ is the y-intercept in a linear equation of the acetone concentration versus the rate of change in colour value. FIG. 6 illustrates Formula (7).

$$CCR=(CC_3-CC_2)/(t_6-t_5) \quad (5)$$

$$MRR=(AC_{max}-AC_{mid})/(CCR_{max}-CCR_{min}) \quad (6)$$

$$AC=M_{CCR}*CCR+ACI_2 \quad (7)$$

The presented system and method can determine the concentration of acetone in the exhaled breath of human. A healthy human can use the system to monitor their rate of burning fat as energy in the body. A human having diabetes can use the system to monitor the change of ketone bodies inside their body. The system is non-invasive and reliable.

The skilled person will appreciate that the examples disclosed herewith with respect to sensors, systems and methods for determining the concentration of carbonyl-containing compound (e.g. acetone) samples could be adapted without undue burden to sensors, systems and methods for determining the concentration of a variety of other analytes.

It will be appreciated that, although specific embodiments of the invention have been described herein for the purpose of illustration, various modifications may be made without deviating from the spirit and scope of the invention as defined in the following claims.

The invention claimed is:

1. A method of determining a concentration of an analyte in a fluid, said method comprising the following steps:

providing a sorbent material having a hydroxylamine salt and a halochromic indicator sorbed thereon, and/or therein, or a combination thereof;

measuring an initial colour value of the sorbent material at an initial time point;

contacting a fluid with the sorbent material to produce a colour change in the sorbent material;

measuring a final colour value of the sorbent material at a final time point; and determining the concentration of analyte in the fluid by:
when a change in colour value of the sorbent material from the initial time point to the final time point is smaller than a threshold colour value:
using the change in colour value of the sorbent material from the initial time point to the final time point; and
when the change in colour value of the sorbent material from the initial time point to the final time point is greater than or equal to the threshold colour value:
using a rate of change in colour value of the sorbent material over a time range, wherein the time range is between the initial time point and the final time point;

wherein:
when the change in colour value of the sorbent material from the initial time point to the final time point is smaller than the threshold colour value, the concentration of analyte is calculated using the equation:

$$AC=M_{CC}*CC+ACI_1,$$

wherein AC is analyte concentration; CC is change in colour value of the sorbent material from the initial time point to the final time point; and $M_{CC}$ is a slope and $ACI_1$ is a y-intercept, respectively, of a standard plot of colour change value of the sorbent material versus analyte concentration; and
when the change in colour value of the sorbent material from the initial time point to the final time point is greater than or equal to the threshold colour value, the concentration of analyte is calculated using the equation:

$$AC=M_{CCR}*CCR+ACI_2,$$

wherein AC is analyte concentration; CCR is rate of change in colour value of the sorbent material over the time range; and $M_{CCR}$ is a slope and $ACI_2$ is a y-intercept, respectively, of a standard plot of rate of colour change value of the sorbent material versus analyte concentration.

2. The method of claim 1, wherein the colour value is an absorbance.

3. The method of claim 1, wherein the colour value is a wavelength.

4. The method of claim 1, wherein the threshold colour value is a colour value corresponding to a concentration of analyte of from about 300 to about 400 ppm (v/v) in the fluid.

5. The method of claim 1, wherein the hydroxylammonium salt is hydroxylammonium chloride.

6. The method of claim 1, wherein the halochromic indicator is selected from the group consisting of methyl orange, methyl red, methyl yellow, methyl green, methyl violet, chlorophenol red, bromocresol green, conga red, thymol blue, bromophenol blue, cresol red, metacresol purple, malachite green, ethyl violet, crystal violet, 2,4-dinitrophenol, orange IV, erythrosin B, p-(phenylazo)diphenylamine, p-phenylazoaniline and mixtures thereof.

7. The method of claim 1, wherein the initial and final colour change values of the sorbent material are measured using a photosensor.

8. The method of claim 1, wherein the method comprises:
collecting a fluid sample from a subject in a vessel;
exposing the sorbent material to a light;
measuring the initial colour value of the sorbent material at the initial time point;
pumping the fluid through a filter to the sorbent material at a constant flow rate;
measuring a second colour value of the sorbent material at a second time point, the second time point being at a time after the initial time point;
measuring a third colour value of the sorbent material at a third time point, the third time point being at a time after the second time point and before the final time point;
ceasing the pumping; and
measuring the final colour value of the sorbent material at the final time point.

9. A system for determining a concentration of an analyte in a fluid, said system comprising:
a vessel receiving unit, capable of receiving a fluid sample vessel;
a sorbent material having a hydroxylamine salt and a halochromic indicator sorbed thereon, and/or therein, or a combination thereof;
a pump for pumping a fluid from the fluid sample vessel to the sorbent material;
a light emitting unit for exposing the sorbent material to a light;
a photosensor for measuring a colour value of the sorbent material at an initial time point and a final time point; and
a control unit, configured to determine the concentration of analyte in the fluid by:
when a change in colour value of the sorbent material from the initial time point to the final time point is smaller than a threshold colour value:
calculating the concentration of analyte using the equation:

$$AC=M_{CC}*CC+ACI_1,$$

wherein AC is analyte concentration; CC is change in colour value of the sorbent material from the initial time point to the final time point; and $M_{CC}$ is a slope and $ACI_1$ is a y-intercept, respectively, of a standard plot of colour change value of the sorbent material versus analyte concentration; and
when the change in colour value of the sorbent material from the initial time point to the final time point is greater than or equal to the threshold colour value:
calculating the concentration of analyte using the equation:

$$AC=M_{CCR}*CCR+ACI_2,$$

wherein AC is analyte concentration; CCR is rate of change in colour value of the sorbent material over the time range; and $M_{CCR}$ is a slope and $ACI_2$ is a y-intercept, respectively, of a standard plot of rate of colour change value of the sorbent material versus analyte concentration.

10. The system of claim 9, wherein the pump is capable of pumping the fluid from the fluid sample vessel to the sorbent material at a constant flow rate.

11. The system of claim 9, further comprising a filter for removing moisture from the fluid.

12. The system of claim 9, wherein the colour value is an absorbance.

13. The system of claim 9, wherein the colour value is a wavelength.

14. The system of claim 9, wherein the hydroxylammonium salt is hydroxylammonium chloride.

15. The system of claim 9, wherein the halochromic indicator is selected from the group consisting of methyl orange, methyl red, methyl yellow, methyl green, methyl violet, chlorophenol red, bromocresol green, conga red, thymol blue, bromophenol blue, cresol red, metacresol purple, malachite green, ethyl violet, crystal violet, 2,4-dinitrophenol, orange IV, erythrosin B, p-(phenylazo)diphenylamine, p-phenylazoaniline and mixtures thereof.

16. The method of claim 1, wherein the fluid is breath.

17. The method of claim 1, wherein the analyte is acetone.

18. A method of managing diabetes in a patient on a diabetes treatment plan, said method comprising:

determining an acetone concentration of a breath sample of the patient using the method of claim 17;

comparing the acetone concentration to a reference acetone concentration range; and if the acetone concentration is outside the acetone concentration reference range, adjusting the diabetes treatment plan.

* * * * *